United States Patent [19]

Kruse et al.

[11] Patent Number: 4,876,266
[45] Date of Patent: Oct. 24, 1989

[54] 1-ARALKYL-2-MERCAPTOIMIDAZOLINES AS DBH INHIBITORS

[75] Inventors: Lawrence I. Kruse, Tewin; Thomas B. Leonard, Letchworth, both of England; Stephen T. Ross, Berwyn, Pa.

[73] Assignee: SmithKline Beckman Corporation, Philadelphia, Pa.

[21] Appl. No.: 140,053

[22] Filed: Dec. 31, 1987

[51] Int. Cl.$^4$ .................. A61K 31/415; C07D 233/42
[52] U.S. Cl. .................................. 514/392; 514/401; 548/317; 548/322; 548/351
[58] Field of Search ...................... 548/351, 317, 322; 514/401, 392

[56] References Cited

U.S. PATENT DOCUMENTS

| | | | |
|---|---|---|---|
| 3,488,423 | 1/1970 | Doebel et al. | 514/392 |
| 3,915,980 | 10/1975 | Gebert et al. | 548/337 |
| 4,532,331 | 7/1985 | Frazee et al. | 548/342 |

FOREIGN PATENT DOCUMENTS

| | | |
|---|---|---|
| 0951 | 3/1979 | European Pat. Off. . |
| 125033 | 11/1984 | European Pat. Off. . |
| 1155580 | 6/1969 | United Kingdom . |
| 2096987 | 10/1982 | United Kingdom . |

OTHER PUBLICATIONS

*Chemical Abstracts*, 105:15302k (1986) [Jpn. Kokai G104,038, Kaneko et al., 1/9/86].
*Chemical Abstracts*, 94:192224m (1981) [Markov, V., et al., *Vopr. Khim. Khim. Tekhnol*, 59, 55 (1980)].
*Chemical Abstracts*, 89:107125j (1978) [Bovin-Roubaud, et al., *C. R. Hebd. Seances Acad. Sci., Ser. C* 1978, 286(20) 521-4].
*Chemical Abstracts*, 86:42591z (1977) [Assef, et al., *C. R. Hebd. Seances Acad. Sci., Ser. C* 1976, 282(11), 485-6].
*Chemical Abstracts*, 78:136299x (1973) [Ger. Offen. 2,140,405, Hiltmann et al., 2/22/73].
*Chemical Abstracts*, 64:15864e (1966) [Cherbuliez et al., *Helv. Chim. Acta* 49(1), 807-31 (1966)].
P. Iversen, et al., *Acta Chem. Scand.*, 21:279-285 (1967).
R. Fuller, et al., *Adv. Enzyme Regul.*, 15:267-281 (1976).
*Chemical Abstracts*, 72:39275e (1970) [Gebert et al., *Hoppe-Seyler's Z. Physiol. Chem.* 1969, 360(11), 1327-30].
J. Bream, et al., *Helv. Chim. Acta*, 60:2872-2880 (1977).

*Primary Examiner*—Richard A. Schwartz
*Attorney, Agent, or Firm*—Mary E. McCarthy; Stuart R. Suter; Alan D. Lourie

[57] ABSTRACT

Disclosed are novel substituted 3-aralkylimidazolines of the structure.

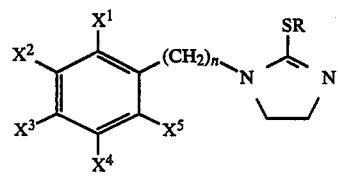

processes for their preparation, intermediates useful in their preparation, pharmaceutical compositions containing them and their use in therapy in particular as dopamine-$\beta$-hydroxylase inhibitors.

15 Claims, No Drawings

1-ARALKYL-2-MERCAPTOIMIDAZOLINES AS DBH INHIBITORS

The present invention relates to novel substituted 1-aralkylimidazoline-2-thiols, processes for their preparation, intermediates useful in their preparation, pharmaceutical compositions containing them and a method of inhibiting dopamine-$\beta$-hydroxylase activity.

Compounds that inhibit DBH activity are well known in the art and include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 1972 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur. J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15 267 (1976)];

(d) substituted thioureas [See, Johnson et al., *J. Pharmacol. Exp. Ther.* 168, 229 (1969)]; and (e) benzyloxamine and benzylhydrazine [See, Creveling et al., *Biochim. Biophys. Acta* 64, 125 (1962); Creveling et al., *Biochim. Biophys. Acta* 8, 215 (1962); Van De Schoot et al., *J. Pharmacol. Exp. Ther.* 141, 74 (1963); Bloom, *Ann N.Y. Acad. Sci.* 107, 878 (1963)].

(f) fusaric acid derivatives and analogues [See, Runti et al., *Il Farmaco Ed. Sci.* 36, 260 (1980)] for example phenylpicolinic acid, 5-(4-chlorobutyl) picolinic acid, substituted amides of fusaric acid and acids and amides of 5-butydropicolinic acid, 5-aminopicolinic acid, 5-hydrazinopicolinic acid, and derivatives thereof.

(g) Hidaka et al., *Molecular Pharmacology*, 9, 172–177 (1972) 5-(3,4-dibromobutyl)picolinic acid and 5-(dimethyldithiocarbamoyl)methylpicolinic acid.

(h) Bupicomide, 5-(n-butyl)picolinamide, is reported by Ehrreich et al., "New Antihypertensive Drugs", Spectrum Publications, 1976, pg. 409–432;

(i) In U.S. Pat. No. 4,532,331 a series of 1-phenyl and 1-phenylalkylimidazole compounds having a mercapto or alkylthio group in the 2-position are disclosed.

(j) U.S. Pat. No. 4,487,761 describes several methylpyridine derivatives isolated from the fermentation broth of a strain of Streptoverticillium.

(k) Friedman et al., Psychosomatic Med. 40, 107 (1978), report that patients treated with alpha-methyl-DOPA, guanethidine, and reserpine, but not propranolol and diuretics, have lowered DBH levels, although the significance of the observation is uncertain.

(l) In U.S. Pat. No. 3,448,423 are disclosed compounds having the formula:

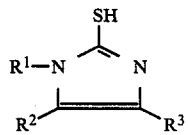

in which
$R^2$ and $R^3$ can be H, and $R^1$ can be substituted phenyl. The compounds are said to have analgesic, anti-inflammatory and antipyretic properties. Gerbert et al., U.S. Pat. No. 3,915,980, disclose such compounds wherein
$R^1$ can be phenyl or phen($C_{1-3}$)alkyl, as intermediates to imidazolyl-2-thioalkanoic acid esters.

(m) Iverson, *Acta Chem. Scan.* 21, 279 (1967) reports compounds having the formula:

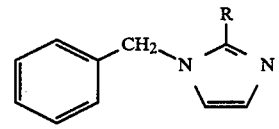

wherein R can be —$CO_2H$ or —$CH_2NHC_6H_5$, but does not report pharmaceutical uses for the compounds.

Therefore there is a continuing need for novel compounds that possess DBH inhibitory activity.

Accordingly the present invention provides compounds of structure (I)

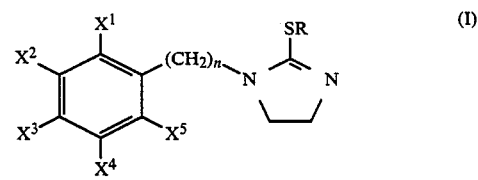

in which, n is 0 to 5;

$X^1$ to $X^5$ are any accessible combination of hydrogen, halogen, $C_{1-6}$alkyl, $C_{1-4}$alkoxy, cyano, nitro, $SONH_2$, $SO_2CH_3$, $SO_2CH_2F$, $SO_2CHF_2$, $SO_2CF_3$, $CF_3$, CHO, OH, $CH_2OH$, $CO_2H$, or $CO_2C_pH_{2p+1}$ wherein p is 1 to 4;

R is hydrogen, $C_{1-4}$alkyl, or $(CH_2)_m$—$CO_2R^1$;

m is 0 to 5; and $R^1$ is H or $C_{1-4}$alkyl; or a pharmaceutically acceptable salt thereof.

As used herein "accessible combination" means any combination of substituents that is available by chemical synthesis and is stable.

It will be appreciated that when R is hydrogen, Structure (I) covers the tautomeric forms thereof that is compounds of structure (Ia).

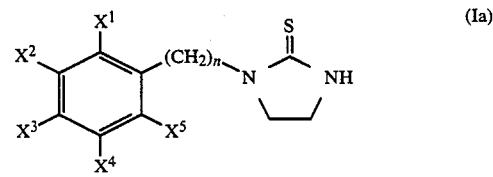

Suitably $X^1$ to $X^5$ are hydrogen.

More suitably at least one of $X^1$ to $X^5$ is halogen and the others are hydrogen. Preferably, one or two of $X^1$ to $X^5$ are halogen. More preferably $X^2$ is halogen and $X^4$ is hydrogen or halogen. Most prefered are compounds in which $X^4$ is fluoro or those in which $X^2$ and $X^4$ are fluoro.

Suitably n is 0 or 2 to 5; preferably n is 1.

Particular compounds of this invention include: 1-(3-fluorobenzyl)-2-mercaptoimidazoline and 1-(3,5-difluorobenzyl)-2-mercaptoimidazoline.

A further aspect of the present invention provides a process for the preparation of compounds of structure (I) and pharmaceutically acceptable salts thereof, which comprises cyclisation of a compound of structure (II)

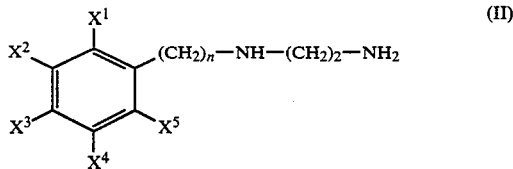

wherein n and $X^1$ to $X^5$ are as defined for structure (IIIa) or (IIIb) in the presence of a reagent which provides a C=S group or cyclisation of a xanthic acid compound of structure (IIIa) or (IIIb)

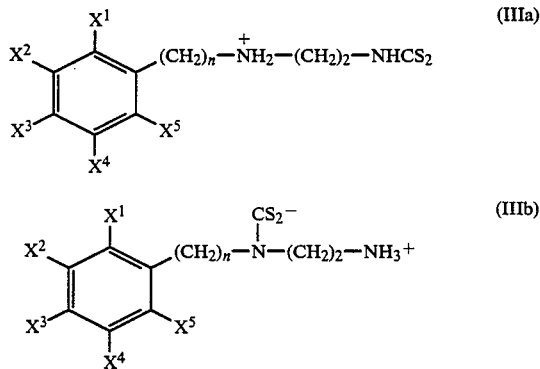

wherein n is 0 to 5, and $X^{1'}$ to $X^{5'}$ are any accessible combination of hydrogen, halogen, $C_{1-6}$alkyl, $C_{1-4}$alkoxy, cyano, nitro, $SONH_2$, $SO_2CH_3$, $SO_2CH_2F$, $SO_2CHF_2$, $SO_2CF_3$, $CF_3$, $CHO$, $CH_2OC_{1-4}$alkyl, $CO_2C_{1-4}$alkyl or $CO_2C_pH_{2p+1}$ wherein p is 1 to 4, and optionally converting $X^{1'}$ to $X^{5'}$ into a hydroxy, $CH_2OH$ or $CO_2H$ group, or converting a compound of structure (I) in which R is hydrogen to one in which R is $C_{1-4}$alkyl or $C_{1-4}$alkanoic acid and optionally forming a pharmaceutically acceptable salt.

Suitable reagents containing a C=S group for cyclization will be apparent to those skilled in the art and include for example thiophosgene in the presence of an aqueous base, suitably sodium carbonate in an inert organic solvent suitably ethyl acetate or toluene. Other suitable C=S containing groups include for example carbon disulphide, diphenylthionocarbonate ($(PhO)_2CS$) and potassium ethyl xanthate ($K^+CS_2OC_2H_5^-$). Other suitable bases include sodium bicarbonate, potassium carbonate or bicarbonate or tertiary amines such as triethylamine. Other suitable inert organic solvents include THF, diethyl ether, dioxane or DMF.

Suitable reagents for the formation of compounds of structure (I) from those of structure (IIIa) or (IIIb) include heating in the presence or absence of an inert organic solvent, for example N-methylpyrrolidone.

Compounds of the invention in which R is $C_{1-4}$alkyl are prepared by alkylating the corresponding compound of structure (I) where R is hydrogen with an alkyl halide in the presence of a base, for example, methyl iodide in methanol in the presence of potassium carbonate, by procedures known to those skilled in the art. Other alkylation reagents such as methyl bromide or dimethyl sulphate, in appropriate solvents in the presence of a base, can be substituted for methyl iodide. Further, the compounds of structure (I) in which R is an alkyl group other than methyl are prepared by substituting an alkyl halide such as butyl iodide, for the methyl halide to yield the desired substituted 1-aralkylimidazoline-2-thiols of the invention.

Compounds of structure (I) in which $R^1$ is $C_{1-4}$alkyl are prepared by reacting the corresponding compound of structure (I) where R is hydrogen with a haloalkanoate ester in the presence of base by procedures known to those skilled in the art, as shown in Example 12. Compounds of structure (I) in which $R^1$ is hydrogen are prepared by mild acid or base hydrolysis of structure (I) compounds in which $R^1$ is $C_{1-4}$alkyl by procedures known to those skilled in the art, as shown in Example 13.

Pharmaceutically acceptable acid addition salts of compounds of the invention are formed with appropriate strong or moderately strong organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention includes maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Pharmaceutically acceptable base addition salts of compounds of the invention containing an acidic group (R is $(CH_2)_m$—$CO_2R^1$ and $R^1$ is H) are prepared by known methods from organic and inorganic bases which include nontoxic alkali metal and alkaline earth bases, for example, calcium, sodium, and potassium hydroxide; ammonium hydroxide; and nontoxic organic bases such as trimethylamine, triethylamine, propylamine, butylamine, piperazine, and (trihydroxymethyl)-methylamine.

Compounds of structure (IIIa) or (IIIb) which are themselves novel and form a further aspect of the invention, can be prepared from compounds of structure (II) by reaction with a reagent containing a CS group (suitably carbon disulphide) in the presence of an inert organic solvent for example ethyl acetate or methanol.

Compounds of structure (II) can in turn be prepared from compounds of structure (IV)

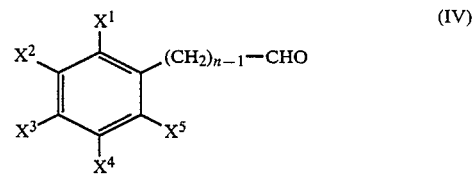

wherein n and $X^1$ to $X^5$ are as defined for structure (III), by reaction with an excess of ethylene diamine followed by addition of a suitable reducing agent, for example, sodium borohydride.

Because the compounds of structure (I) inhibit DBH activity, they have therapeutic value as diuretic, natriuretic, cardiotonic, antihypertensive, and vasodilator agents, as well as antiulcerogenic and anti-Parkinson agents. Listed in Table III are the compounds of the invention that were tested for in vitro DBH inhibition by a standard procedure for assaying conversion of tyramine to octopamine in the presence of DBH. J. J. Pisano, et al., *Biochim. Biophys. Acta,* 43, 566–568 (1960). Octopamine was assayed following sodium periodate oxidation to p-hydroxybenzaldehyde by measuring spectrophotometric absorbance at 330 nm. In Table III, inhibition is given in micromolar concentration of compound at which DBH activity was halved ($IC_{50}$). By this test, fusaric acid had an $IC_{50}$ of 0.8 micromolar.

TABLE III

| Compound | DBH $IC_{50}$ ($\mu M$) |
|---|---|
| 1-Benzyl-2-mercaptoimidazoline | 10 |
| 1-(3-Fluorobenzyl)-2-mercaptoimidazoline | 3.7 |
| 1-(3,5-Difluorobenzyl)-2-mercaptoimidazoline | 1.2 |

Further, spontaneously hypertensive rats were treated with a suspension or solution of 1-(3,5-difluorobenzyl)-2-mercaptoimidazoline at a dose of 50 mg/kg orally and mean arterial blood pressure was monitored for 260 minutes using indwelling cannulae in the tail arteries. When compared to vehicle-treated controls, animals treated with the compounds of the invention exhibited significant blood pressure reductions within approximately 30 minutes after treatment. Maximum blood pressure reduction was approximately 15 to 20 mm Hg.

The present invention thus also provides a method of inhibiting DBH activity which comprises administering to a mammal, including a human, an effective amount of a compound of structure (I) or a pharmaceutically acceptable salt thereof.

The present invention additionally provides a method of producing lower blood pressure in mammals, including humans, that comprises administering an effective amount of a compound of Structure (I) or a pharmaceutically acceptable salt thereof.

In the methods of the present invention the compounds of structure (I) are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier. Such compositions include those suitable for administration via an appropriate route known to those skilled in the art for example, orally, parenterally, transdermally, rectally, via inhalation or via buccal administration.

The compounds of structure (1) and their pharmaceutically acceptable salts which are active when given orally can be formulated as tablets, capsules, lozenges and liquids, for example syrups, suspensions or emulsions.

A liquid formulation will generally consist of a suspension or solution of the compound or pharmaceutically acceptable salt in a suitable liquid carrier(s) for example, ethanol, glycerine, sorbitol, non-aqueous solvent, for example polyethylene glycol, oils, or water with a suspending agent, preservative surfactant, wetting agent, flavouring or colouring agent.

Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid formulations. Examples of such carriers include magnesium stearate, starch, lactose, sucrose, cellulose and binders, for example, polyvinyl, pyrrolidone. The tablet can also be provided with a colour film coating, or colour included as part of the carrier(s). In addition, acting compound can be formulated in a controlled release dosage form as a tablet comprising a hydrophilic or hydrophobic matrix.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Compounds of structure (I) and their pharmaceutically acceptable salts which are active on topical administration can be formulated as transdermal compositions. Such compositions include, for example, a backing, active compound reservoir, a control membrane, liner and contact adhesive.

Typical compositions for inhalation are in the form of a solution, suspension or emulsion that may be administered in the form of an aerosol using a conventional propellant such as dichlorodifluoromethane or trichlorofluoromethane.

Preferably the composition is in an appropriate unit dosage form. Each dosage unit for oral administration contains preferably from 1 to 250 mg (and for parenteral administration contains preferably from 0.1 to 25 mg) of a compound of structure (I) or a pharmaceutically acceptable salt thereof calculated as the free acid.

The daily dosage regimen for an adult patient may be, for example, an oral dose of between 1 mg and 1000 mg, preferably between 1 mg and 250 mg, or an intravenous, subcutaneous, or intramuscular dose of between 0.1 mg and 100 mg, preferably between 0.1 mg and 25 mg, of the compound of structure (I) or a pharmaceutically acceptable salt thereof calculated as the free base, the compound being administered 1 to 4 or more times per day. Suitably the compounds will be administered for a period of continuous therapy, for example for a week or more. In addition, the compounds of this invention may be co-administered with other pharmaceutically active compounds, for example in combination, concurrently or sequentially.

The following Examples illustrate the invention. Temperatures are recorded in degrees centigrade.

EXAMPLE 1

N-Benzylethylenediamine

A 20.0 g (0.189 mol) quantity of benzaldehyde was added dropwise with stirring to 45.3 g (0.754 mol, 4/1 molar ratio) of ethylene diamine which had been dissolved in 500 ml methanol and the solution chilled to 0° C. After the benzaldehyde addition was complete, a 7.13 g (0.189 mol) quantity of sodium borohydride was added in small portions as a solid maintaining the temperature at 0±2° C. The reaction mixture was allowed to stir overnight and warm to ambient temperature. The resulting cloudy solution was filtered and the filtrate was concentrated to a heavy oil. The oil was triturated with water and the mixture extracted three times with ethyl acetate. Concentration of the combined ethyl acetate extracts gave 25.9 g of oil. This was vacuum distilled to give 19.05 g (67% yield) of desired product, b.p. 78°–84° C. at 79.99 to 106.66 Nm$^{-2}$ (Newton milimeters).

EXAMPLE 2

N-(3-Fluorobenzyl)ethylanediamine

A 23.4 g (0.189 mol) quantity of 3-fluorobenzaldehyde was treated by the same procedure as used for N-benzylethylenediamine (Example 1) to give 21.6 g (68% yield) of the desired product, b.p. 89°–91° C. at 93.33 Nm$^{-2}$.

EXAMPLE 3

N-(3,5-Difluorobenzyl)ethylenediamine

At 16.77 g (0.118 mol) quantity of 3,5-difluorobenzaldehyde was treated with 50 ml ethylenediamine and 4.47 g (0.118 mol) sodium borohydride in 500 ml methanol by the method prescribed for N-benzylethylenediamine (Example 1) to give 12.0 g (55% yield) of desired product, b.p. 90°–92° C. at 199.98–226.65 Nm$^{-2}$.

EXAMPLE 4

N-(3-Fluorobenzyl)ethylenediamine Xanthic Acid

A 5.0 g (0.030 mol) quantity of N-(3-fluorobenzyl)-ethylenediamine (Example 2) was dissolved in 50 ml ethyl acetate and the solution chilled to 0° C. A 2.26 g (0.030 mol) portion of carbon disulfide dissolved in 10 ml ethyl acetate was added dropwise with stirring. The solution became opaque and a small amount of precipitate formed. This was filtered and the filtrate concentrated to give 6.28 g of desired product as a white solid (87% yield).

EXAMPLE 5

N-(3,5-Difluorobenzyl)ethylene Xanthic Acid

A 5.0 g (0.027 mol) quantity of N-(3,5-difluorobenzyl)ethylenediamine (Example 3) was dissolved in 50 ml methanol, the solution chilled to 0° C. and 2.04 g (0.027 mol) of carbon disulfide was added with stirring. The mixture was allowed to warm to ambient temperature and stir overnight and a white crystalline solid formed. This was filtered to give 4.9 g (69% yield) of desired product.

EXAMPLE 6

1-Benzyl-2-mercaptoimidazoline

Solutions of 10.9 g (0.067 mol) N-benzylethylenediamine (Example 2) and 7.65 g (0.067 mol) thiophosgene, each dissolved in 50 ml toluene, were added dropwise and concurrently to a stirred mixture of 14.1 g (0.133 mol) sodium carbonate dissolved in 100 ml water and 100 ml toluene which had been chilled to 0° C. After the 20–30 minute addition period the reaction mixture was allowed to warm to ambient temperature and stirring was continued at this temperature for one hour. The reaction mixture was filtered and the insoluble solid, 7.2 g, was recrystallized twice from methanol-ethyl acetate to give 2.25 g (18% yield) of desired product, m.p. 177°–182° C.

EXAMPLE 7

1-(3-Fluorobenzyl)-2-mercaptoimidazoline

A 5.73 g (0.024 mol) quantity of N-(3-fluorobenzyl)ethylenediamine xanthic acid (Example 4) was heated neat in an oil bath at 165° C. Melting, intumescence and resolidification began to occur. The mixture was further heated to 185° C. and 5 ml N-methylpyrrolidone was added to complete the reaction. Heating was continued for a few minutes and the reaction mixture was then allowed to cool. The resulting mixture of crystalline solid and liquid was stirred with ethyl acetate and the solution filtered to give 2.3 g of solid. An addition 2.1 g of crystalline solid was obtained by concentration of the filtrate. The combined solid was recrystallized from methanol-chloroform to give 3.15 g of desired product (64% yield), m.p. 186°–188° C.

EXAMPLE 8

1-(3,5-Difluorobenzyl)-2-mercaptoimidazoline

A 4.75 g (0.018 mol) quantity of N-(3,5-difluorobenzyl)ethylenediamine xanthic acid (Example 5) was heated neat in an oil bath at 170° C. The solid gradually melted with the evolution of hydrogen sulfide. The temperature of the oil bath was raised to 200° C. and heating continued for 15–20 minutes. The resulting yellow oil was cooled and spontaneously crystallized. The solid was recrystallized from chloroform-methanol to give 3.5 g (85% yield) of desired product, m.p. 286°–187° C. with softening at 185° C.

EXAMPLE 9

1-(2-Nitrobenzyl)-2-mercaptoimidazoline

The processes of Examples 1 through 6 in which benzaldehye is replaced by 2-nitrobenzaldehyde yields 1-(2-nitrobenzyl)-2-mercaptoimidazoline.

EXAMPLE 10

1-(3-Cyanophenethyl)-2-mercaptoimidazoline

The processes of Examples 1 through 6 in which benzaldehyde is replaced by 2-cyanophenylacetaldehyde yields 1-(3-cyanophenethyl)-2-mercapto-imidazoline.

EXAMPLE 11

1-(2-Methyl-3-fluoro-5-chlorobenzyl)-2-mercaptoimidazoline

The processes of Examples 1 through 6 in which benzaldehyde is replaced by 2-fluoro-4-chlorotoluene yields 1-(2-methyl-3-fluoro-5-chlorobenzyl)-2-mercapto-imidazoline.

EXAMPLE 12

2-(2-Carbomethoxyethylthio)-1-(3,5-difluorobenzyl)imidazoline 1-(3,5-difluorobenzyl)-2-mercaptoimidazoline, prepared as in example 8, and potassium hydroxide in equimolar proportions in dimethylformamide and water are stirred under argon at ambient temperature, and one mole of methyl-3-bromopropionate is added. The reaction mixture is heated at 95° C. overnight, cooled, and extracted three times with ether, and the combined ether extracts are concentrated. Purification by flash chromatography on silica gel gives 2-(2-carbomethoxyethylthio)-1-(3,5-difluorobenzyl)imidazoline.

EXAMPLE 13

2-(2-Carboxyethylthio)-1-(3,5-difluorobenzyl)imidazoline 2-(2-Carbomethoxyethylthio)-1-(3,5-difluorobenzyl)imidazoline prepared as in example 12 is stirred with aqueous sodium hydroxide and the reaction mixture is heated at reflux for one hour, cooled, and neutralized with concentrated hydrochloric acid. The mixture then is extracted three times with ether and the combined ether extracts are concentrated. Trituration of the residue with boiling hexane and recrystallization from ethylacetate-hexane, yields 2-(2-carboxyethylthio)-1-(3,5-difluorobenzyl)imidazoline.

EXAMPLE 14

An oral dosage form for administering the presently invented compounds is produced by screening, mixing, and filling into hard gelatin capsules the ingredients in the proportions shown in Table I, below.

TABLE I

| Ingredients | Amounts |
|---|---|
| 1-(3,5-Difluorobenzyl)-2-mercaptoimidazoline | 50 mg |
| magnesium stearate | 5 mg |
| lactose | 75 mg |

EXAMPLE 15

The sucrose, calcium sulfate dihydrate, and structure I compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
|---|---|
| 1-(3-Fluorobenzyl)-2-mercaptoimidazoline | 100 mg |
| calcium sulfate dihydrate | 150 mg |
| sucrose | 20 mg |
| Starch | 10 mg |
| talc | 5 mg |
| stearic acid | 3 mg |

EXAMPLE 16

1-(3-Fluorobenzyl)-2-mercaptoimidazoline hydrochloride, 75 mg, is dispursed in 25 ml of normal saline to prepare an injectable preparation.

Contemplated equivalents of compounds of structure I are compounds that upon administration to mammals, including humans, are metabolized to compounds of structure I or metabolized to any active metabolites of compounds of structure I at a sufficient rate and in sufficient amounts to produce the physiological activity of compounds of structure I. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

We claim:
1. A compound of the formula:

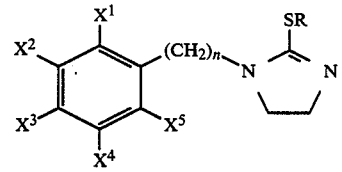

in which:

n is 1 to 5;

$X^1$ to $X^5$ are any accessible combination of hydrogen, halogen, $C_{1-6}$alkyl, $C_{1-4}$alkoxy, cyano, nitro, $SONH_2$, $SO_2CH_3$, $SO_2CH_2F$, $SO_2CHF_2$, $SO_2CF_3$, $CF_3$, $CHO$, $OH$, $CH_2OH$, $CO_2H$, or $CO_2C_pH_{p+1}$ wherein p is 1 to 4;

R is hydrogen, $C_{1-4}$alkyl or $(CH_2)_m$—$CO_2R^1$;

m is 0 to 5; and $R^1$ is H or $C_{1-4}$alkyl; or a pharmaceutically acceptable salt thereof, provided that when n is 1 to 5 and $X^1$ to $X^5$ are all hydrogen, R is not hydrogen.

2. A compound of claim 1 in which n is 1.

3. A compound as claimed in claim 2 in which one or two of $X^1$ to $X^5$ is halogen.

4. A compound as claimed in claim 2 in which $X^4$ is halogen or $X^4$ and $X^2$ are halogen.

5. A compound as claimed in claim 4 that is 1-(3-fluorobenzyl)-2-mercaptoimidazoline.

6. A compound as claimed in claim 4 in that is 1-(3,5-difluorobenzyl)-2-mercaptoimidazoline.

7. A pharmaceutical composition having dopamine-β-hydroxylase inhibiting activity comprising an effective amount of a compound of the formula:

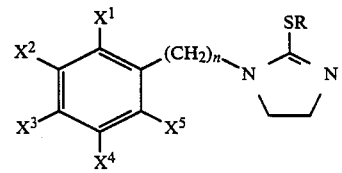

in which:

n is 1 to 5;

$X^1$ to $X^5$ are any accessible combination of hydrogen, halogen, $C_{1-6}$alkyl, $C_{1-4}$alkoxy, cyano, nitro, $SONH_2$, $SO_2CH_3$, $SO_2CH_2F$, $SO_2CHF_2$, $SO_2CF_3$, $CF_3$, $CHO$, $OH$, $CH_2OH$, $CO_2H$, or $CO_2C_pH_{p+1}$ wherein p is 1 to 4;

R is hydrogen, $C_{1-4}$alkyl or $(CH_2)_m$—$CO_2R^1$;

m is 0 to 5; and $R^1$ is H or $C_{1-4}$alkyl, and a pharmaceutically acceptable carrier.

8. A composition of claim 7 in which the compound is 1-(3-fluorobenzyl)-2-mercaptoimidazoline.

9. A composition of claim 7 in which the compound is 1-(3,5-fluorobenzyl)-2-mercaptoimidazoline.

10. A method of inhibiting DBH activity in a subject which comprises administering to a subject an effective amount of a compound as claimed in claim 1.

11. A method of claim 10 in which the compound is 1-(3-fluorobenzyl)-2-mercaptoimidazoline.

12. A method of claim 10 in which the compound is 1-(3,5-difluorobenzyl)-2-mercaptoimidazoline.

13. A method of producing lower blood pressure in a subject which comprises administering to a subject an effective amount of a compound as claimed in claim 1.

14. The method of claim 13 in which the compound is 1-(3-fluorobenzyl)-2-mercaptoimidazoline.

15. The method of claim 13 in which the compound is 1-(3,5-difluorobenzyl)-2-mercaptoimidazoline.

* * * * *